(12) United States Patent
Tsukagoshi et al.

(10) Patent No.: US 7,715,519 B2
(45) Date of Patent: May 11, 2010

(54) X-RAY COMPUTED TOMOGRAPHY APPARATUS AND IMAGE PROCESSING APPARATUS

(75) Inventors: Shinsuke Tsukagoshi, Nasushiobara (JP); Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 100 days.

(21) Appl. No.: 12/177,393

(22) Filed: Jul. 22, 2008

(65) Prior Publication Data
US 2009/0028409 A1 Jan. 29, 2009

(30) Foreign Application Priority Data
Jul. 24, 2007 (JP) ............... 2007-192257

(51) Int. Cl.
*A61B 6/03* (2006.01)

(52) U.S. Cl. ............ 378/4; 378/901; 382/131; 600/425

(58) Field of Classification Search ............ 378/4, 378/901; 382/131; 600/425
See application file for complete search history.

(56) References Cited

U.S. PATENT DOCUMENTS

| | | | |
|---|---|---|---|
| 6,249,693 B1 * | 6/2001 | Cline et al. | 600/410 |
| 6,628,743 B1 * | 9/2003 | Drummond et al. | 378/8 |
| 7,529,396 B2 * | 5/2009 | Matsumoto | 382/128 |
| 2006/0071932 A1 * | 4/2006 | Weese et al. | 345/424 |

FOREIGN PATENT DOCUMENTS

JP 2003-190148 7/2003

* cited by examiner

*Primary Examiner*—Allen C. Ho
(74) *Attorney, Agent, or Firm*—Oblon, Spivak, McClelland, Maier & Neustadt, L.L.P.

(57) ABSTRACT

An X-ray tube generates X-rays. An X-ray detector detects X-rays generated from the X-ray tube and transmitted through an object to be examined. A rotating frame continuously rotates the X-ray tube and the X-ray detector around the object. A reconstruction unit reconstructs a plurality of first volume data sets with different scan times for the same scan area of the object on the basis of an output from the X-ray detector. An image processing unit generates single second volume data set corresponding to a maximum value, an average value, a median value, or minimum value of the plurality of reconstructed first volume data sets in the temporal direction.

15 Claims, 11 Drawing Sheets

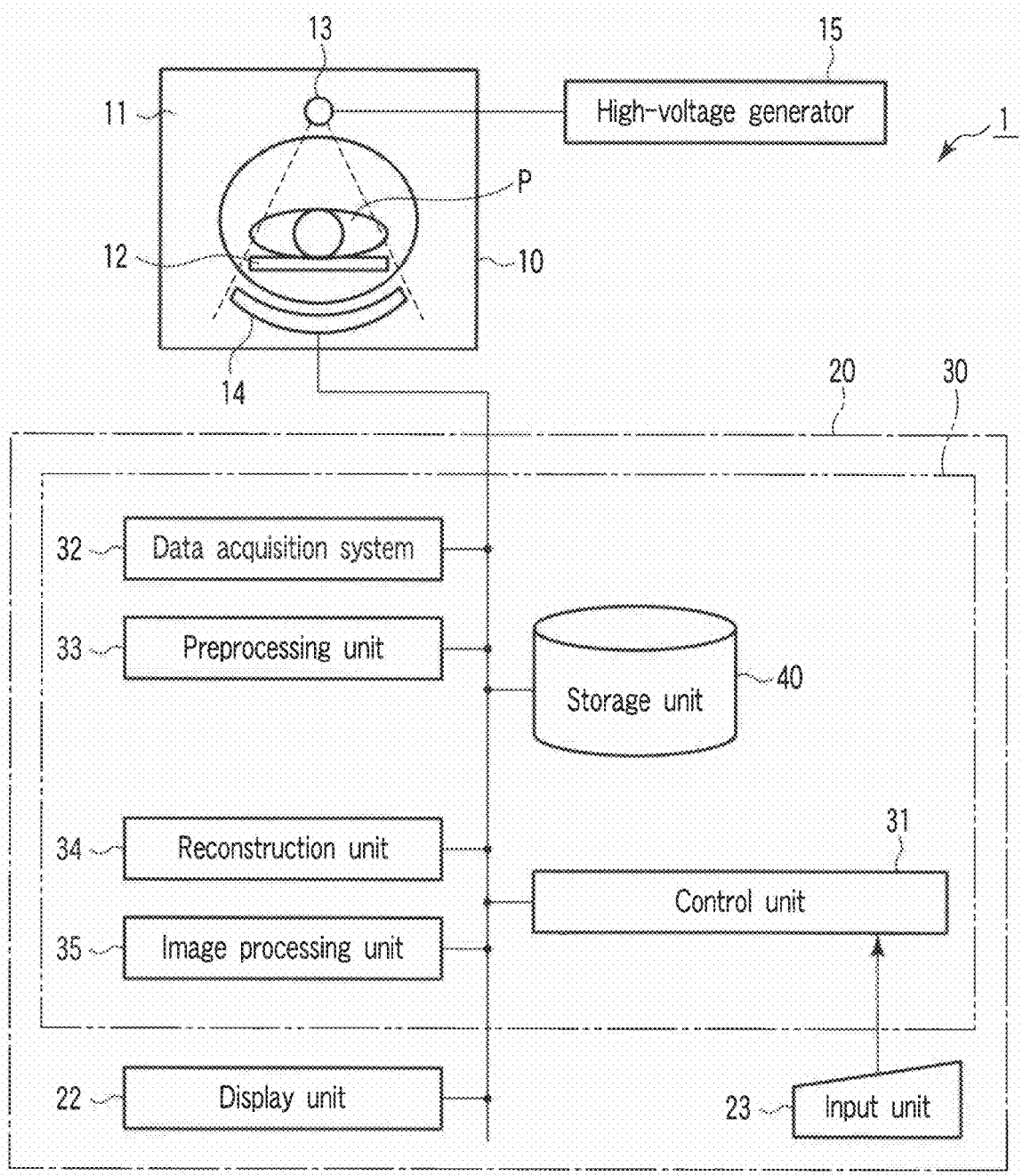
F I G. 1

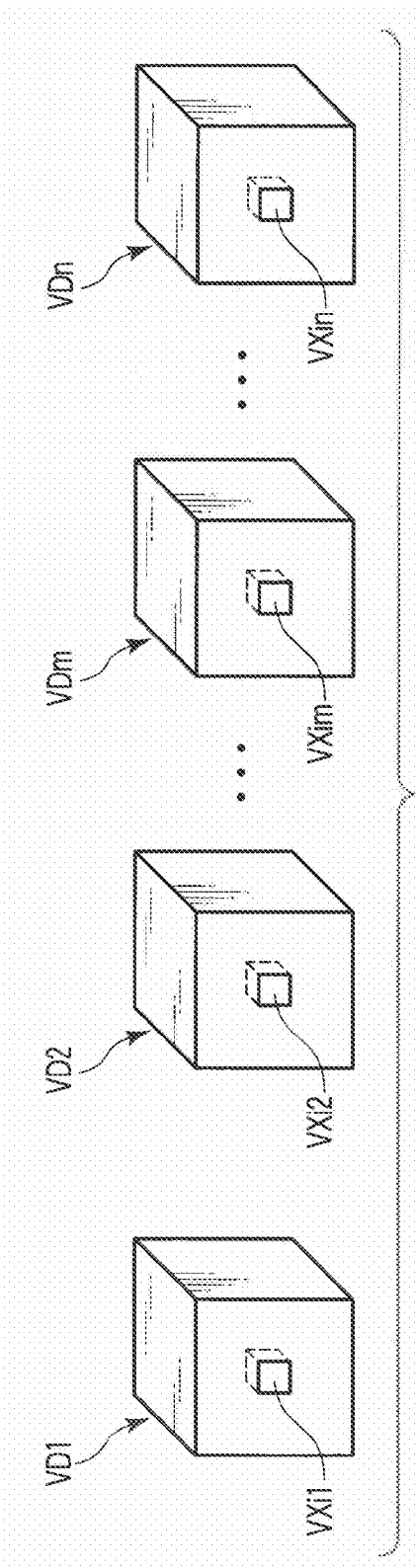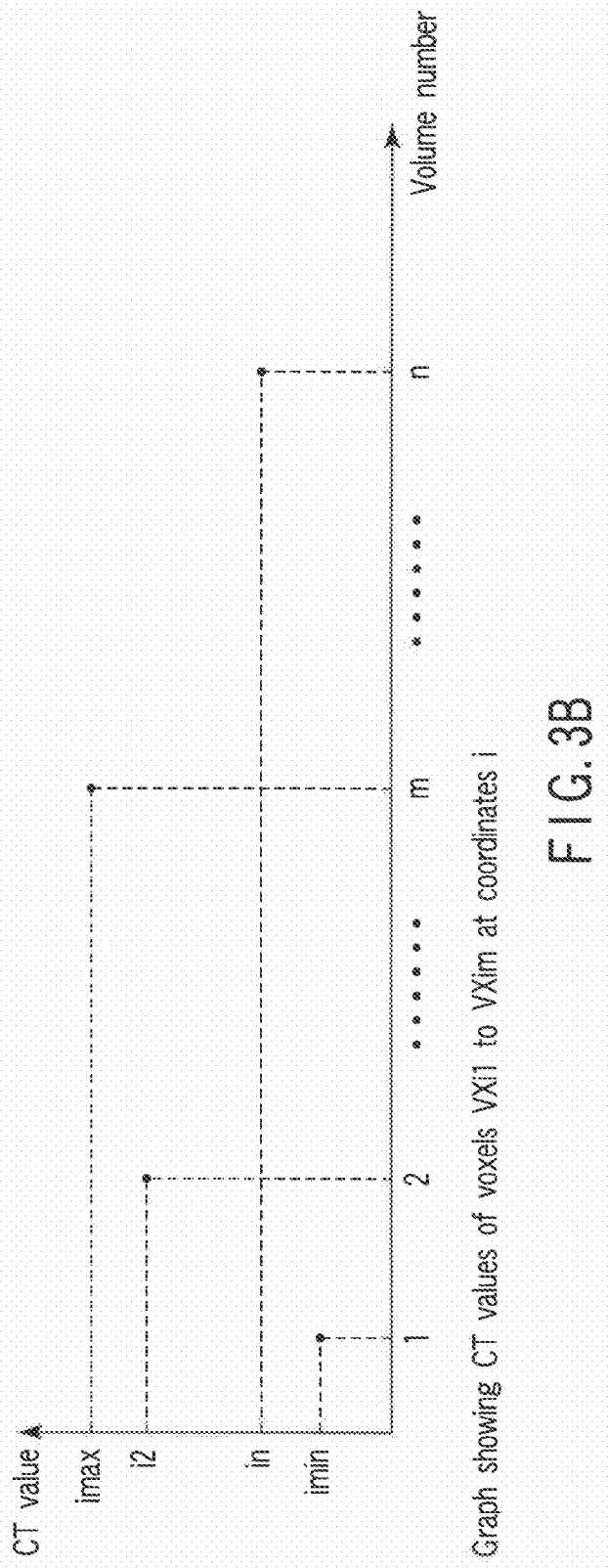

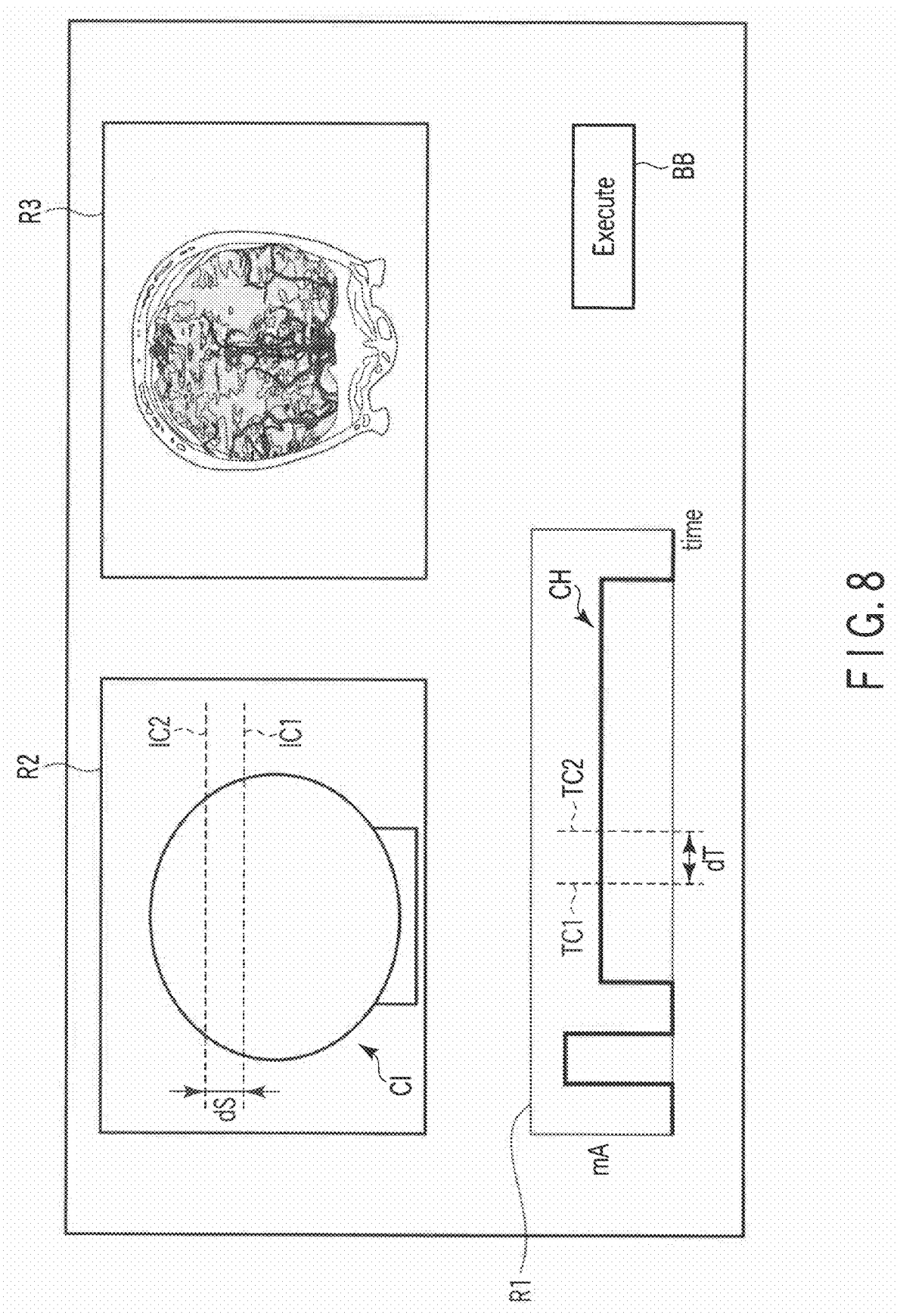
F I G. 8

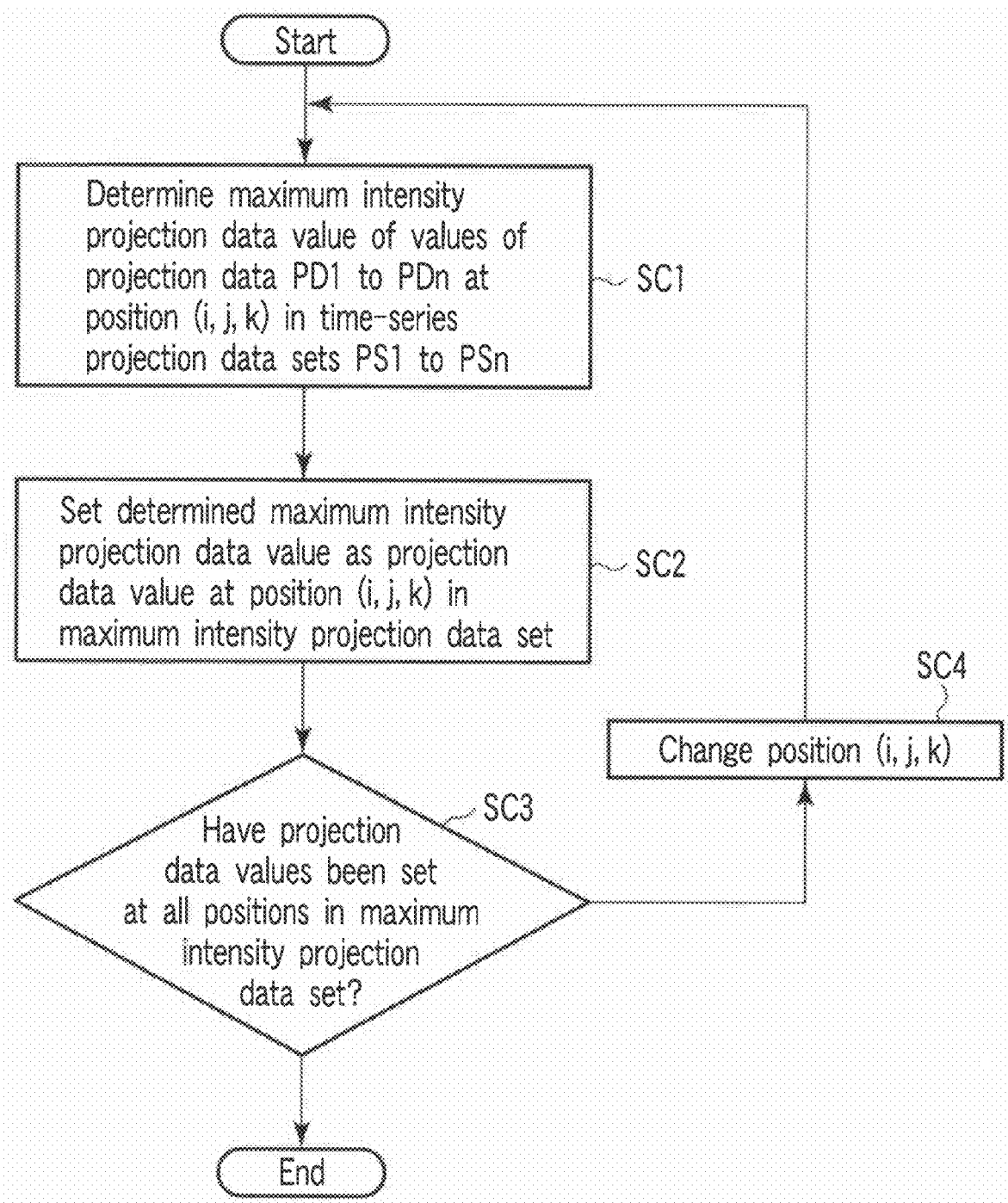
F I G. 10

X-RAY COMPUTED TOMOGRAPHY APPARATUS AND IMAGE PROCESSING APPARATUS

CROSS-REFERENCE TO RELATED APPLICATIONS

This application is based upon and claims the benefit of priority from prior Japanese Patent Application No. 2007-192257, filed Jul. 24, 2007, the entire contents of which are incorporated herein by reference.

BACKGROUND OF THE INVENTION

1. Field of the Invention

The present invention relates to an X-ray computed tomography apparatus and image processing apparatus which generate a plurality of volume data sets with different scan times for the same scan area of an object to be examined.

2. Description of the Related Art

In an X-ray computed tomography apparatus, a technique called a 4DCT scan is available to generate a plurality of volume data sets with different scan times for the same scan area. Recently, this 4DCT scan can superimpose a blood vessel image and a functional image for a blood flow (perfusion). This superimposition processing is useful for image diagnosis. A blood vessel image concerns a time (e.g., a time near a peak of a TDC) at which a blood vessel is imaged most clearly by CT angiography (CTA). A functional image is calculated on the basis of a plurality of volume data sets. More specifically, a functional image is generated by calculating an index (e.g., a CBP, CBV, or MTT) indicating the blood flow dynamic state of tissue (e.g., brain tissue) for each voxel and assigning pixels pieces of color information corresponding to the calculated index values (see, for example, Jpn. Pat. Appln. KOKAI Publication No. 2003-190148).

When a blood vessel image is to be generated, since different volume data sets to be processed exhibit different blood flow dynamic states, the user needs to designate optimal positions (or ranges) for blood vessel image generation for all the volume data sets. In addition, when blood vessel image data is generated on the basis of the volume data set, of all the volume data sets, which concern a predetermined period of time, the generated blood vessel image does not contain any information about a blood vessel at which a contrast agent has not arrived within the predetermined period of time. This causes a phenomenon in which the blood vessel is not imaged even after the function is restored.

When function analysis based on TDC (e.g., an algorithm such as the deconvolution method) is to be executed on the basis of a plurality of volume data sets with different scan times, since the amount of data to be processed is large, a problem arises in terms of processing time.

BRIEF SUMMARY OF THE INVENTION

It is an object of the present invention to provide an X-ray computed tomography apparatus and image processing apparatus which can improve the efficiency of diagnosis based on a plurality of volume data sets.

An X-ray computed tomography apparatus according to a first aspect of the present invention, comprising: an X-ray tube which generates X-rays; an X-ray detector which detects X-rays generated from the X-ray tube and transmitted through an object to be examined; a rotating mechanism unit which continuously rotates the X-ray tube and the X-ray detector around the object; a reconstruction unit which reconstructs a plurality of first volume data sets with different scan times for the same scan area of the object on the basis of an output from the X-ray detector; and an image processing unit which generates single second volume data set corresponding to one of a maximum value, an average value, a median value, and minimum value of the plurality of reconstructed first volume data sets in a temporal direction.

An X-ray computed tomography apparatus according to a second aspect of the present invention, comprising: an X-ray tube which generates X-rays; an X-ray detector which detects X-rays generated from the X-ray tube and are transmitted through an object to be examined; a rotating mechanism unit which continuously rotates the X-ray tube and the X-ray detector around the object; a reconstruction unit which reconstructs a plurality of first volume data sets with different scan times for the same scan area of the object on the basis of an output from the X-ray detector; and an image processing unit which generates single second volume set data by processing the plurality of reconstructed first volume data sets.

An X-ray computed tomography apparatus according to a third aspect of the present invention, comprising: an X-ray tube which generates X-rays; an X-ray detector which detects X-rays generated from the X-ray tube and are transmitted through an object to be examined; a rotating mechanism unit which continuously rotates the X-ray tube and the X-ray detector around the object; a first projection data generation unit which generates a plurality of first projection data sets with different scan times for the same scan area of the object on the basis of an output from the X-ray detector; a second projection data generation unit which generates a single second projection data set corresponding to one of a maximum value, an average value, a median value, and a minimum value of the plurality of generated first projection data sets in a temporal direction; and a reconstruction unit which reconstructs volume data set on the basis of the generated second projection data set.

An image processing apparatus according to a fourth aspect of the present invention, comprising: a storage unit which stores a plurality of first volume data sets with different scan times for the same scan area of an object to be examined; and an image processing unit which generates single second volume data set corresponding to one of a maximum value, an average value, a median value, and a minimum value of the plurality of first volume data sets in a temporal direction.

An image processing apparatus according to a fifth aspect of the present invention, comprising: a storage unit which stores a plurality of first projection data sets with different scan times which are generated by continuously scanning the same scan area of an object to be examined; a projection data processing unit which generates a single second projection data set corresponding to one of a maximum value, an average value, a median value, and a minimum value of the plurality of first projection data sets in a temporal direction; and a reconstruction unit which reconstructs volume data set for the object on the basis of the generated second projection data set.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodi- FIG. 1 is a block diagram showing the arrangements of an X-ray computed tomography apparatus and image processing apparatus according to the first embodiment of the present invention;

FIG. 3A is a view for explaining the processing in steps SA1 and SA2 in FIG. 2;

FIG. 3B is another view for explaining the processing in steps SA1 and SA2 in FIG. 2;

FIG. 8 is a view showing a window interface for designating the range of projection processing for the temporal direction and the range of projection processing for the spatial direction with respect to the image processing unit in FIG. 1;

FIG. 10 is a flowchart showing the sequence of maximum intensity projection data set generation processing by a projection data processing unit in FIG. 9.

DETAILED DESCRIPTION OF THE INVENTION

Figure 2:
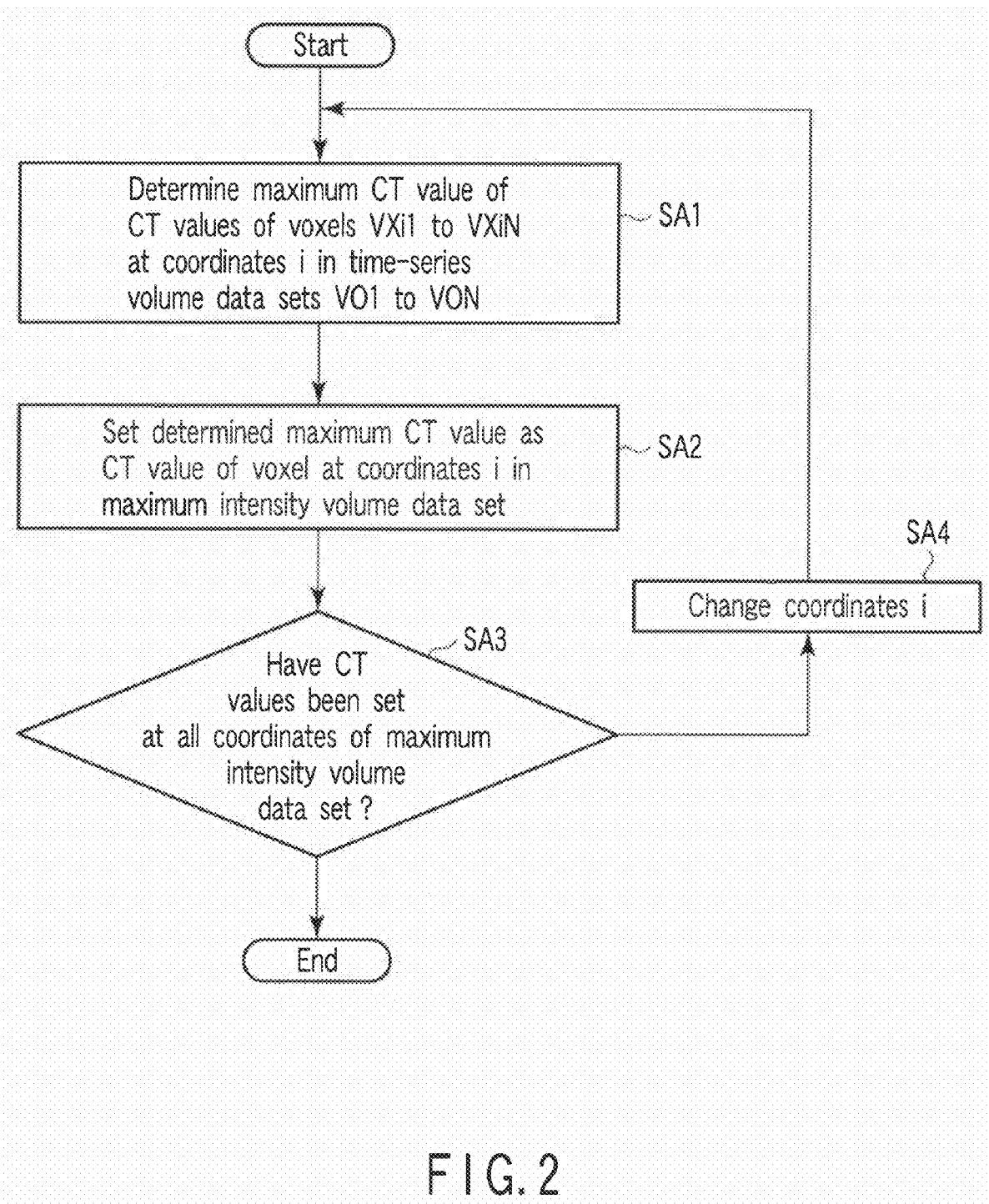
FIG. 2 is a flowchart showing the sequence of maximum intensity volume data set generation processing by an image processing unit in FIG. 1.

The first and second embodiments of the present invention will be described below with reference to the views of the accompanying drawing.

First Embodiment

FIG. 1 is a block diagram showing the arrangement of an X-ray computed tomography apparatus (referred to as an X-ray CT apparatus hereinafter) 1 according to the first embodiment. The X-ray CT apparatus 1 includes a gantry 10 and a computer apparatus 20. The gantry 10 rotatably supports an annular or disk-like rotating frame 11. The rotating frame 11 has an X-ray tube 13 and an X-ray detector 14 which face each other through an object P placed on a top 12 in an imaging area. The rotating frame 11 continuously rotates the X-ray tube 13 and the X-ray detector 14 at a predetermined angular velocity. The X-ray tube 13 generates X-rays upon receiving a high voltage and filament current from a high-voltage generator 15. Typically, the X-ray tube 13 generates cone beam X-rays having a large cone angle and generally having a quadrangular pyramidical shape. A data acquisition system (DAS) 32 is connected to the X-ray detector 14. The X-ray detector 14 has a plurality of detection elements densely distributed in both the row direction and the channel direction. An array composed of a plurality of detection elements in a line along the channel direction will be referred to as a detection element array. A plurality of detection element arrays are arranged along the row direction (the body axis direction of the object). For example, 320 detection element arrays are arranged in the row direction.

The computer apparatus 20 comprises an image processing apparatus 30, a display unit 22, and an input unit 23. The display unit 22 displays images. The input unit 23 inputs instructions from the user to the computer apparatus 20. The image processing apparatus 30 includes a control unit 31 as a main unit, the data acquisition system 32, a preprocessing unit 33, a reconstruction unit 34, an image processing unit 35, and a storage unit 40.

The data acquisition system 32 amplifies a current signal read out from the X-ray detector 14 for each channel and converts the current signal into a digital signal. The data output from the data acquisition system 32 reflects the intensities of incident X-rays and is called raw data.

The preprocessing unit 33 performs processing such as logarithmic conversion or sensitivity correction of the X-ray detector 14 for the raw data output from the data acquisition system 32. The data output from the preprocessing unit 33 is called projection data. The projection data is stored in the storage unit 40.

The reconstruction unit 34 generates volume data set for a specific imaging region of the object by performing image reconstruction processing for the projection data from the storage unit 40. In the first embodiment, a 4DCT scan (continuously scanning the same scan area) is performed under the control of the control unit 31. The reconstruction unit 34 generates a plurality of volume data sets with different scan times (referred to as time-series volume data sets hereinafter). Note that the voxel values of the plurality of time-series volume data sets are CT values. Note that the reconstruction unit 34 can perform filter processing or the like for the reduction of noise in images. The plurality of reconstructed time-series volume data sets are stored in the storage unit 40 in association with codes representing the respective scan times.

The image processing unit 35 has a time-series projection function, a space projection function, a color information assignment function, a tomogram generation function, a time density curve generation function, a functional image generation function, and a blood vessel extraction function. Each function will be described below.

With the time-series projection function, the image processing unit 35 generates single volume data set corresponding to the maximum value, average value, median value, or minimum value of a plurality of time-series volume data sets with different scan times in the temporal direction. For example, the image processing unit 35 generates single maximum intensity volume data set from a plurality of time-series volume data sets. More specifically, the image processing unit 35 compares a plurality of voxel values at the same position in a plurality of time-series volume data sets and specifies a maximum value among the plurality of voxel values. The specified maximum value is set as the voxel value of the maximum intensity volume set at the same position. The maximum intensity volume data set is generated by performing this processing at each position. Note that "position" in this case means the coordinates of time-series volume data sets and maximum intensity volume set.

In the space projection processing (rendering) function, the image processing unit 35 generates display image data corresponding to the maximum value, average value, median value, or minimum value of maximum intensity volume data set or time-series volume data sets in the spatial direction. More specifically, the image processing unit 35 generates the data of a maximum intensity projection image, minimum intensity projection image, median intensity projection image, or average intensity projection image by performing maximum intensity projection, minimum intensity projection, median intensity projection, or average intensity projection of the maximum intensity volume data set or time-series volume data sets from a desired projection point along a projection locus. Space projection processing need not be performed for an entire volume set. That is, space projection processing can be slab maximum intensity projection (slab MIP), slab average intensity projection, slab median intensity projection, slab minimum intensity projection, or the like. The display unit 22 displays various images generated by the space projection processing.

In the color information assignment processing, the image processing unit 35 generates the data of a color image by assigning color information to each voxel or pixel constituting maximum intensity volume data set or tomographic data. The display unit 22 displays the color image generated by the color information assignment processing.

In the tomogram generation processing, the image processing unit 35 generates tomographic data for a slice at an arbitrary position and in an arbitrary direction for volume data set.

In the time density curve generation processing, the image processing unit 35 generates a time density curve for a specific area of a plurality of time-series volume data sets.

With the functional image generation function, the image processing unit 35 generates the data of a functional image having a two- or three-dimensional map of index values such as CBP (a blood flow amount [ml/100 ml/min] per unit volume and unit time in a capillary vessel of brain tissue) values representing the blood flow dynamic state of a brain tissue portion, CBV (blood flow amount [ml/100 ml] per unit volume in brain tissue) values, or MTT (blood mean transit time [sec] in a capillary vessel) values on the basis of a plurality of time-series volume data sets. This index value is calculated as follows. First of all, the image processing unit 35 calculates a temporal change in the density of a contrast agent in a region of interest set in a cerebral artery portion of an image and a temporal change in the density of the contrast agent in a brain tissue portion of the image. The image processing unit 35 calculates a transfer function which associates the calculated change in density in the cerebral artery portion with the calculated change in density in the brain tissue portion. The image processing unit 35 then calculates the above index value from the calculated transfer function. The details of this operation are described in, for example, patent reference 1.

With the blood vessel extraction function, the image processing unit 35 extracts the data of a blood vessel portion by performing threshold processing or the like for maximum intensity volume data set, display image data, or the like.

The X-ray CT apparatus 1 having the above arrangement performs a 4DCT scan (continuously scanning the same scan area) under the control of the control unit 31. For a concrete description, assume that a scan target is the head portion of the object.

When the head portion is to be scanned to check a blood flow dynamic state, a line connecting the orbit and the external acoustic pore, i.e., an orbitomeatal (OM) line is set as a reference for positioning, as is well known. Typically, the head portion is positioned such that this OM line and the vertex are included in the scan area. The distance between this OM line and the vertex varies among individuals. In the case of adults, however, the distances are generally almost 12 to 14 cm. In the case of children, the distances are generally 8 cm or more. The X-ray detector 14 comprises 320 detection element arrays. The length of a scan area in the slice direction which the X-ray detector 14 can cover is generally 16 cm. That is, using the X-ray detector 14 can acquire all projection data necessary to reconstruct the entire scan area by only performing a 4DCT scan while rotating the X-ray tube 13 and the X-ray detector 14 at a fixed position without moving the top 12 or the gantry 10.

The reconstruction unit 34 generates a plurality of time-series volume data sets of the object on the basis of a plurality of projection data sets generated by such a 4DCT scan. During the 4DCT scan, the object is fixed, and the top 12 and the gantry 10 do not move. The plurality of time-series volume data sets generated by the 4DCT scan are therefore positioned to each other. Assume that time-series volume data set is a rectangular parallelepiped comprising L×M×N voxels. L, M, and N are arbitrary numbers.

Maximum intensity volume data set generation processing by the image processing unit 35 will be described in detail below. The image processing unit 35 generates a plurality of time-series volume data sets VD1 to VDn which concern the head portion of the object and are temporally continuous. Assume that a 4DCT scan is performed immediately after or before the injection of a contrast agent. This time-series volume data set is image data representing a temporal change in the density of a contrast agent in the object. Note that the subscripts 1 to n satisfy condition 1<n, and indicate the times (order) of generation. These subscripts will be referred as volume numbers. The volume number 1 indicates the time immediately after or before the injection of a contrast agent, and the volume number n indicates the time when the contrast agent flowing in the head portion is sufficiently diluted. Voxels corresponding to time-series volume data set VD1, VD2, . . . , VDn at coordinates i are written as voxels VXi1, VXi2, . . . , VXin, respectively.

FIG. 2 is a flowchart showing the sequence of maximum intensity volume data set generation processing. First of all, upon receiving a start request from the input unit 23 or the like, the control unit 31 causes the image processing unit 35 to perform maximum intensity volume data set generation processing. In the maximum intensity volume data set generation processing, first of all, the image processing unit 35 reads the plurality of time-series volume data sets VD1 to VDn from the reconstruction unit 34 or the storage unit 40. The image processing unit 35 then determines a predetermined CT value on the basis of the CT values of the voxels VXi1 to VXin at the coordinates i in the plurality of read time-series volume data sets VD1 to VDn (step SA1). For example, the predetermined CT value is the maximum value (maximum CT value) of the CT values of the voxels VXi1 to VXin.

The maximum CT value determined in step SA1 is set as the CT value of the voxel at the coordinates i in the maximum intensity volume data set at the coordinates i in a mathematical three-dimensional space defined in a memory in the image processing unit 35 or the like (step SA2).

FIGS. 3A and 3B are views for concretely explaining the processing in steps SA1 and SA2. FIG. 3A is a view showing voxels VXi1 to VXin at the coordinates i (e.g., [x, y, z]=[0, 0, 0]). As shown in FIG. 3A, the voxels VXi1 to VXin are all voxels at the same coordinates i, although they were generated at different times (volume numbers). First of all, the CT values of the voxels VXi1 to VXin at the coordinates i (e.g., [x, y, z]=[0, 0, 0]) in the plurality of time-series volume data sets VD1 to VDm to VDn (1<m<n) are specified. The maximum CT value of the specified plurality of CT values is specified. The specified maximum CT value is set as the CT value at the coordinates i in the maximum intensity volume data set. In the case shown in FIG. 3B, a CT value imax of the voxel VXim of the time-series volume data set VDm is maximum, and the CT value imax is set as the CT value at the coordinates i in the maximum intensity volume data set.

When the processing in step SA2 is complete, the image processing unit 35 determines whether CT values have been set at all the coordinates (all coordinates [0, 0, 0] to [L, M, N]) of the maximum intensity volume data set (step SA3). In step SA4, if NO is determined (NO in step SA3), the image processing unit 35 changes the coordinates i (step SA4). The image processing unit 35 then performs the processing in steps SA1 and SA2 at the coordinates set after the coordinate change. When the image processing unit 35 completes the processing at all the coordinates (YES in step SA3), CT values are set at all the coordinates of the maximum intensity volume data set. That is, the maximum intensity volume data set is generated. When the maximum intensity volume data set is generated, the maximum intensity volume data set generation processing is terminated.

In the above maximum intensity volume data set generation processing, the image processing unit 35 generates the maximum intensity volume data set by processing the plurality of time-series volume data sets VD1 to VDn.

Figure 4:
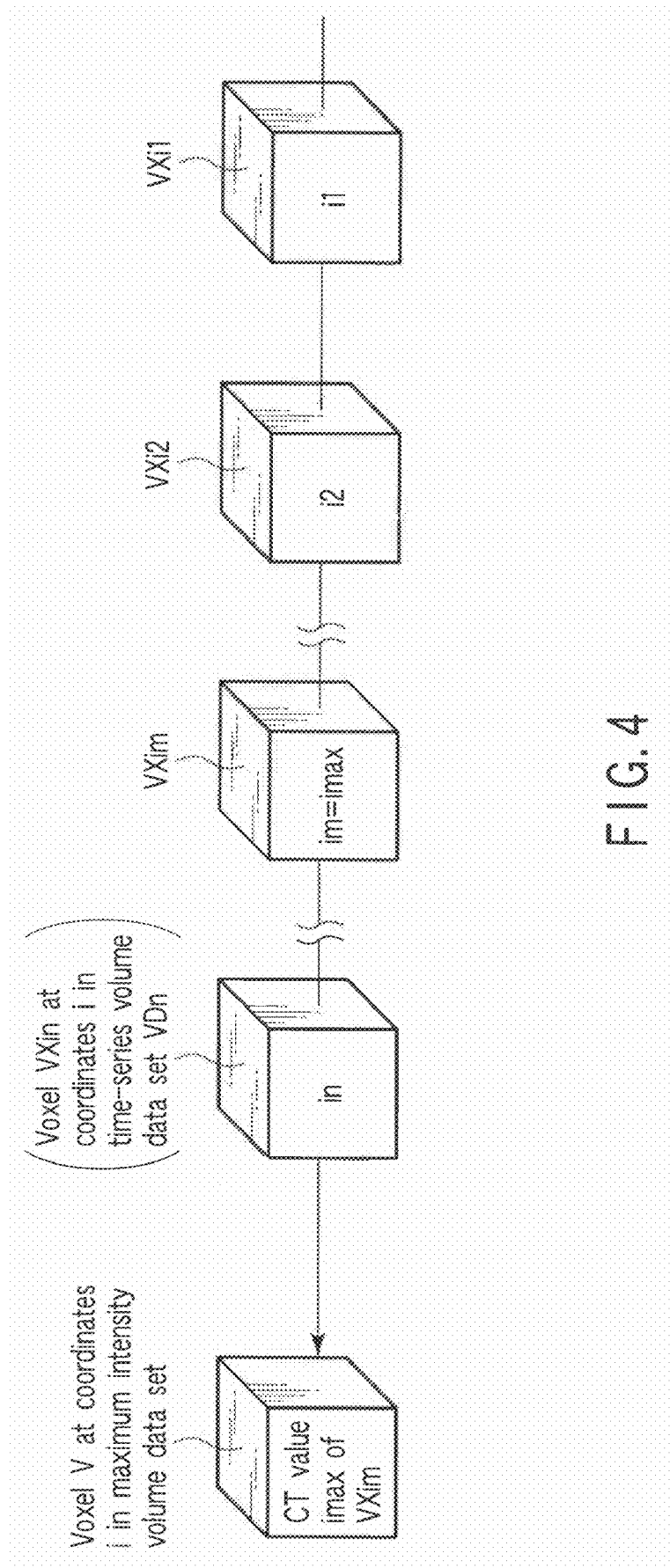
FIG. 4 is a view for explaining maximum intensity volume data set generation processing by the image processing unit in FIG. 1.

As shown in FIG. 4, the maximum intensity volume data set generation processing can be regarded as a new method of converting four-dimensional image data (the plurality of time-series volume data sets VD1 to VDn) into single three-dimensional image data (maximum intensity volume data set). More specifically, this processing is a method of setting, as the CT value of a voxel V at the coordinates i in the maximum intensity volume data set, the maximum CT value imax of the CT values of the voxels VXi1 to VXin at the same coordinates i in the plurality of volume data sets VD1 to VDn. According to this idea, the maximum intensity volume data set generation processing can be regarded as time-series MIP processing.

As described above, maximum intensity volume data set contains information about a delay blood vessel at which a contrast agent arrives late relative to a blood vessel at which the contrast agent arrives earlier, because the maximum intensity volume data set is based on all the time-series volume data sets generated by 4DCT. Furthermore, since the maximum intensity volume data set is generated on the basis of the maximum CT value, a blood vessel portion imaged in the data has better contrast than a blood vessel portion imaged in volume data set generated by time-series adding/averaging processing. Note that the time-series adding/averaging processing is the processing of setting the average of the sum of the CT values of the voxels VXi1 to VXin at the same coordinates i in the time-series volume data sets VD1 to VDn as the CT value of a voxel at the coordinates i in the maximum intensity volume data set.

According to the above description, time-series MIP processing is performed at all the coordinates of volume data sets. However, the processing to be performed need not be limited to this. This processing can be performed for only a specific area such as a blood vessel portion, brain tissue, an approximately spherical area including the center of volume data sets, or a cubic area.

In step SA2, a predetermined CT value is set as the maximum value of the CT values of a plurality of voxels. However, the predetermined CT value may be a minimum value, an average value, or the like. Alternatively, the predetermined CT value may be the CT value of a morbid portion such as a tumor or a calcification.

An application of the first embodiment will be described next along the sequence of processing shown in FIG. 5. First of all, the control unit 31 reads out a plurality of time-series volume data sets with different scan times for the same scan area from the reconstruction unit 34 or the storage unit 40 (step SB1). The control unit 31 then determines whether to designate a time-series volume set to be processed by maximum intensity volume data set generation processing (step SB2).

Upon receiving a designation request from the input unit 23 or the like, the control unit 31 causes the image processing unit 35 to perform time density curve generation processing. In the time density curve generation processing, the image processing unit 35 generates a time density curve (TDC) for a specific area (e.g., an artery portion) of a plurality of time-series volume data sets by using a known technique (step SB3). Note that a time density curve is a curve which represents a temporal change in CT value in specific areas of a plurality of time-series volume data sets. The control unit 31 causes the display unit 22 to display the generated time density curve. When the time density curve is displayed, the control unit 31 waits until the user designates the time range (period) of time-series volume data sets to be processed by maximum intensity volume data set generation processing through the input unit 23. The user can discriminate an arterial phase or a venous phase by observing the time density curve. When, for example, the user designates a time range corresponding to an arterial phase, the obtained maximum intensity volume data set mainly images an artery portion.

When the user designates the time range of time-series volume data sets through the input unit 23, the control unit 31 causes the image processing unit 35 to perform maximum intensity volume data set generation processing. The image processing unit 35 generates maximum intensity volume data set by performing maximum intensity volume data set generation processing for the time-series volume data sets designated in step SB3 or all the time-series volume data sets (step SB5). The maximum intensity volume data set generation processing is the same as the above method. Note that when the time range of time-series volume data sets to be processed is designated, it suffices to set the above time-series volume data sets VD1 to VDn as time-series volume data set in the designated range.

When the maximum intensity volume data set is generated, the control unit 31 causes the image processing unit 35 to generate the data of a tomogram of a desired slice (step SB6). When the data of the tomogram is generated, the control unit 31 causes the image processing unit 35 to perform blood vessel extraction processing. In the blood vessel extraction processing, the image processing unit 35 extracts a blood vessel portion from the tomogram by performing threshold processing for the tomogram with a CT value which discriminates a blood vessel portion and other portions being set as a threshold (step SB7). When the blood vessel portion is extracted, the control unit 31 causes the image processing unit 35 to perform color information assignment processing. In the color information assignment processing, the image processing unit 35 assigns color information to each pixel corresponding to the blood vessel portion (step SB8). Color information is, for example, a single color such as red.

The control unit 31 also causes the image processing unit 35 to perform functional image generation processing in a step other than steps SB6 to SB8. In the functional image generation processing, the image processing unit 35 generates the data of a functional image of the same slice as that in step SB7 by using a known technique (see, e.g., patent reference 1) on the basis of a plurality of time-series volume data sets (step SB9). A functional image is an image which is obtained by calculating an index value for a blood flow for each voxel on the basis of a plurality of time-series volume data sets and assigning color information to each voxel in accordance with each calculated index value. For example, as an index for a blood flow, CBP [ml/100 ml/min], CBV [ml/100 ml], MTT [sec], or the like can be suitably used. Since a method of generating a functional image for such an index is the same as that described in Jpn. Pat. Appln. KOKAI Publication No. 2003-190148, a description of the method will be omitted.

Figure 6:
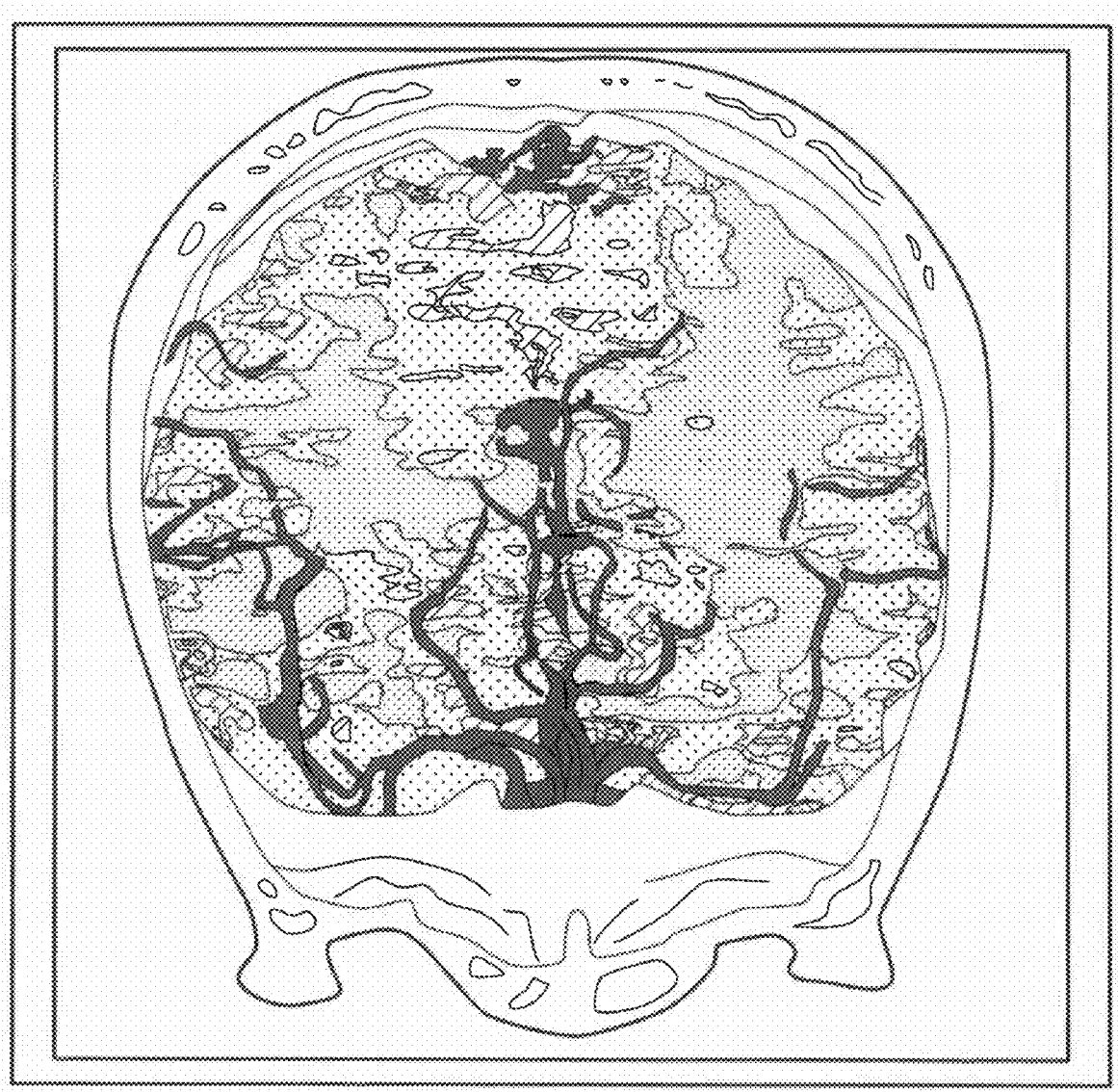
FIG. 6 is a view showing an image displayed in step SB10 in FIG. 5.

When steps SB8 and SB9 are complete, the control unit 31 causes the display unit 22 to superimpose and display the blood vessel portion and the functional image in color (step SB10). FIG. 6 is a view showing an example of the image displayed in step SB1. As shown in FIG. 6, the imaged brain tissue portion is displayed in different colors in accordance with the index values. In addition, since the blood vessel portion originates from the maximum intensity volume data set, the blood vessel portion is imaged in good contrast with the running state of blood vessels being clearly imaged.

Figure 5:
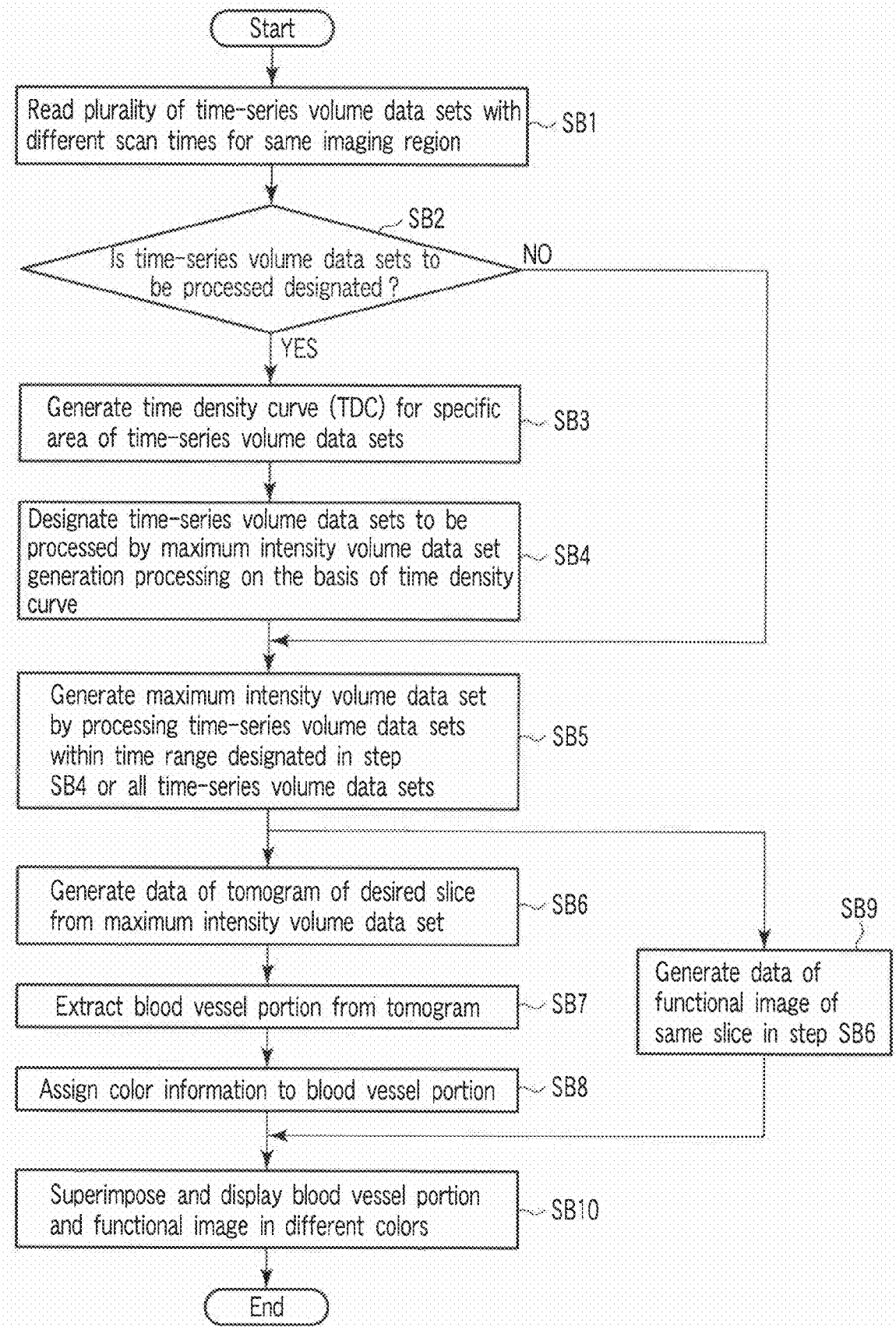
FIG. 5 is a flowchart showing the sequence of maximum intensity volume data set generation processing according to an application of the first embodiment.

The sequence of processing shown in FIG. 5 is terminated with the above operation.

As another application of the first embodiment, the blood vessel portion and brain tissue portion contained in the maximum intensity volume data set can be displayed in color with color information being assigned to each portion. In this case, the image processing unit 35 assigns color information to a voxel comprising maximum intensity volume data set such that the blood vessel portion and brain tissue portion contained in the maximum intensity volume data set are discriminated from each other. More specifically, the brain tissue portion is a capillary vessel portion running in the brain tissue, and the blood vessel portion is a blood vessel portion other than the capillary vessel, e.g., a cerebral artery or a cerebral vein.

Figure 7:
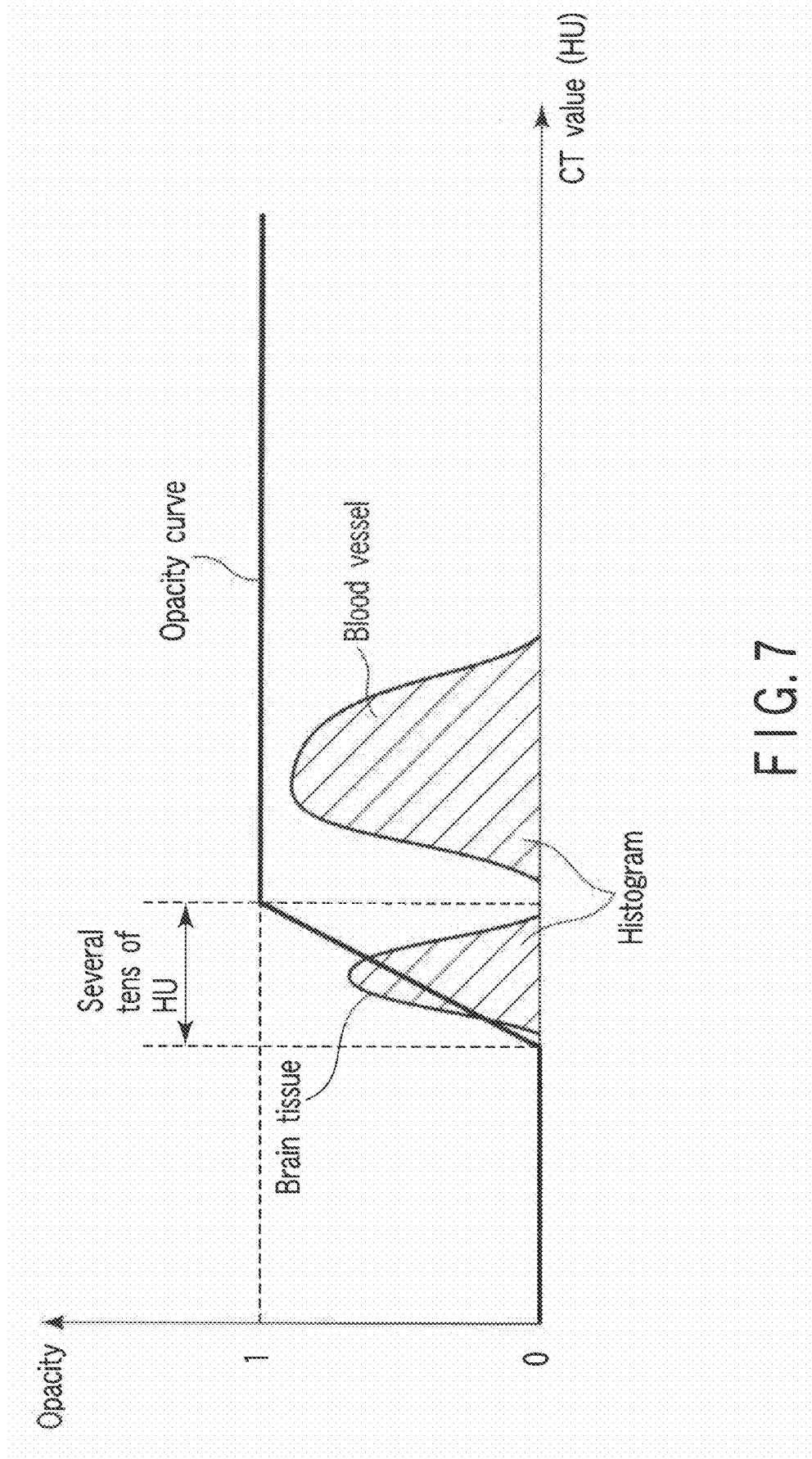
FIG. 7 is a graph showing color information assignment processing for maximum intensity volume data set according to another application of the first embodiment.

Color information assignment processing in another application will be described with reference to FIG. 7. FIG. 7 is a graph showing an opacity curve and a histogram which indicates the relationship between the CT values and the opacities assigned to voxels of the maximum intensity volume data set. In general, the range of CT values which can be regarded as the CT values of brain tissue is as narrow as several tens of HU. The opacity "1" is assigned to a voxel (blood vessel portion) having a CT value higher than the maximum CT value of the brain tissue, and the opacity "0" is assigned to a voxel (water or a fat portion [not shown]) having a CT value smaller than the minimum CT value of the CT values of the brain tissue. Opacities are assigned to the voxels of the brain tissue portion such that the opacities linearly change from "0" to "1" in accordance with the CT values. Color information is assigned to each voxel in accordance with the opacity which the voxel has. More specifically, one color such as red is assigned to a blood vessel portion, and about eight colors other than red are assigned stepwise to a brain tissue portion in accordance with the opacities. No color information is assigned to voxels other than those of the blood vessel portion and brain tissue portion.

The brain tissue portion imaged in the tomogram based on the maximum intensity volume data set assigned with color information in this manner is displayed in different colors in accordance with the CT values. The brain tissue portion in the maximum intensity volume data set has the maximum CT value of the time-series CT values at the corresponding coordinates. Observing a tomogram originating from the maximum intensity volume data set allows the user to determine the blood flow information of the brain tissue in accordance with the color information. That is, this tomogram can be used as a blood vessel image indicating the running state of blood vessels and a functional image of the brain tissue.

With the above arrangement, the X-ray CT apparatus 1 generates single volume data set on the basis of a plurality of volume data sets. According to a given aspect, simply observing only a single image based on generated single volume data set allows the user to obtain the same effect as that obtained when he/she observes a plurality of images based on a plurality of volume data sets. According to the first embodiment, therefore, the efficiency of diagnosis based on a plurality of volume data sets can be improved.

Note that the present invention is not limited to the above embodiment, and constituent elements can be variously modified and embodied at the execution stage within the spirit and scope of the invention. Various inventions can be formed by proper combinations of a plurality of constituent elements disclosed in the above embodiment. For example, several constituent elements may be omitted from the all the constituent elements in the embodiment.

The display unit 22 can also display a window interface which makes the image processing unit 35 selectively execute projection processing for the temporal direction or projection processing concerting the spatial direction. This window interface includes a display area for a volume data set list, a time-series projection processing button, and a space projection processing button. In the list display area, a plurality of volume data sets as processing target candidates are displayed. For example, in the list display area, information about a maximum intensity volume set and information about a plurality of time-series volume data sets are displayed. The information of the plurality of time-series volume data sets is displayed, for example, for each series or studies. The time-series projection processing button is a button for performing time-series projection processing for volume data sets to be processed. The space projection processing button is a button for performing space projection processing for volume data set to be processed. When, for example, the user selects a plurality of time-series volume data sets through the input unit 23 and presses the time-series projection processing button, the image processing unit 35 performs time-series projection processing for the selected plurality of time-series volume data sets.

The display unit 22 may also display a window interface for designating at least one of the range of projection processing for the temporal direction and the range of projection processing for the spatial direction with respect to the image processing unit 35. FIG. 8 is a view showing a display example of this window interface. As shown in FIG. 8, the window interface includes a designation area R1, a designation area R2, an execution button BB, and a display area R3. The designation area R1 is an area for designating a range for the temporal direction. More specifically, in the designation area R1, a time chart CH and two cursors TC1 and TC2 are displayed. The time chart CH represents a scan sequence as a temporal change in tube current. The two cursors TC1 and TC2 are cursors for designating a time range on the time chart CH. A range dT defined by the two cursors TC1 and TC2 is set as a time range in the time projection processing. The designation area R2 is an area for designating a range for the spatial direction. More specifically, in the designation area R2, a tomogram CI and two cursors IC1 and IC2 are displayed. The tomogram CI is an image for the time range designated by the cursors TC1 and TC2. The tomogram CI is an image for an axial slice, a coronal slice, a sagittal slice, or an arbitrary slice. The two cursors IC1 and IC2 are cursors for designating a space range on the tomogram CI. A range dS defined by the two cursors IC1 and IC2 is set as a space range in space projection processing. When the user presses the execution button BB through the input unit 23, the image processing unit 35 performs projection processing in the designated time range and space range. In the display area R3, the image generated by the projection processing in the designated time range and space range is displayed.

Assume that the scan area which is 4DCT-scanned by the X-ray CT apparatus 1 is the head portion of the object. However, the portion to be scanned is not limited to this, and any region other than the head portion can be set as a scan area. In order to make full use of the characteristic of the X-ray detector 14, i.e., that the X-ray detector 14 comprises a plurality of detection element arrays, the scan area is preferably a large internal organ such as the liver which has a length of 8 cm or more in the slice direction while the object is placed on the top 12. This is because, since the X-ray CT apparatus 1 can perform a 4DCT scan on the entire large internal organ without moving the top 12 or the gantry 10, as described above, positioning is not required for a plurality of time-series volume data sets generated by the 4DCT scan.

Second Embodiment

Figure 9:
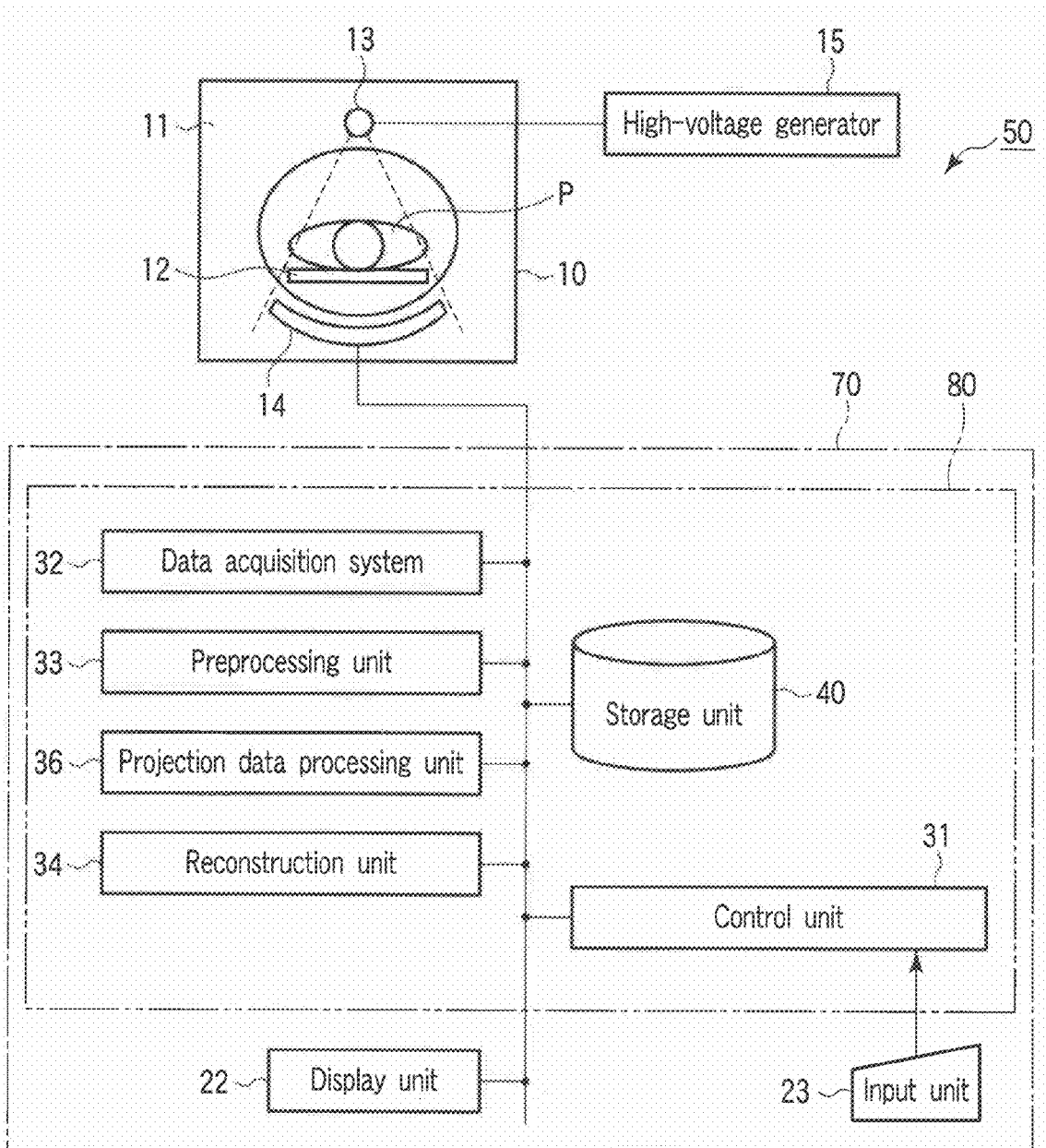
FIG. 9 is a block diagram showing an X-ray computed tomography apparatus and image processing apparatus according to the second embodiment of the present invention.

FIG. 9 is a block diagram showing the arrangement of an X-ray CT apparatus 50 according to the second embodiment of the present invention. Note that the same reference numbers denote constituent elements having substantially the same functions as in the first embodiment, and a repetitive description will be made only when required.

As shown in FIG. 9, the X-ray CT apparatus 50 includes a gantry 10 and a computer apparatus 70. The computer apparatus 70 comprises an image processing apparatus 80, a display unit 22, and an input unit 23. The image processing apparatus 80 includes a control unit 31 as a main unit, a data acquisition system 32, a preprocessing unit 33, a reconstruction unit 34, a projection data processing unit 36, and a storage unit 40.

The data acquisition system 32 amplifies the current signal read out from each detection element of an X-ray detector 14 and converts the current signal into a digital signal. The data output from the data acquisition system 32 reflects the intensities of incident X-rays and is called raw data.

The preprocessing unit 33 performs processing such as logarithmic conversion or sensitivity correction of the X-ray detector 14 for the raw data output from the data acquisition system 32. The data output from the preprocessing unit 33 is called projection data. In this case, a set of projection data required to reconstruct one volume data set will be regarded as one unit and referred to as a projection data set. In the second embodiment as well, a 4DCT scan is performed under the control of the control unit 31. The preprocessing unit 33 generates a plurality of projection data sets (time-series projection data sets) with different scan times for the same scan area. The plurality of generated time-series projection data sets are stored in the storage unit 40 in association with codes representing the scan times. A time-series projection data set is, for example, the time when the X-ray tube 13 is positioned at a rotational angle of 0°. The position of each projection data is defined by the view number (the rotational angle of the X-ray tube) and the position of the detection element corresponding to the projection data (the channel number and the row number).

The projection data processing unit 36 generates a single projection data set corresponding to the maximum value, average value, median value, or minimum value of a plurality of projection data sets in the temporal direction. For example, the projection data processing unit 36 generates a single maximum intensity projection data set from a plurality of projection data sets. More specifically, the projection data processing unit 36 compares the values of a plurality of projection data at the same position (the number of view, the number of channels, and the number of rows) on a plurality of projection data sets, and specifies the maximum value of the values of the plurality of projection data. The projection data processing unit 36 sets the specified maximum value as the value of projection data at the same position in the maximum intensity projection data set. The projection data processing unit 36 generates a maximum intensity projection data set by performing this processing at each position. The generated projection data set is stored in the storage unit 40.

The reconstruction unit 34 generates maximum intensity volume data set, average intensity volume data set, median intensity volume data set, or minimum intensity volume data set by performing reconstruction processing for a maximum intensity projection data set, an average intensity projection data set, a median intensity projection data set, or a minimum intensity projection data set. The storage unit 40 stores the generated volume data set.

Maximum intensity projection data set generation processing by the projection data processing unit 36 will be described in detail below. A plurality of time-series projection data sets PS1 to PSn which concern the head portion of the object and are temporally continuous are generated by 4DCT. Assume that a 4DCT scan is performed immediately after or before the injection of a contrast agent. These subscripts will be referred to as projection data set numbers. Note that the projection data set numbers 1 to n satisfy condition 1<n, and indicate the times (order) of generation. The projection data set number 1 indicates the time immediately after or before the injection of a contrast agent. The projection data set number n indicates the time when the contrast agent flowing in the head portion is sufficiently diluted. Projection data at the positions (view, channel, row) of time-series projection data sets PS1, PS2, . . . , PSn are respectively written as projection data PD1 (view, channel, row), PD2 (view, channel, row), . . . , PDn (view, channel, row).

As described above, during a 4DCT scan, the object is fixed, and the top 12 and the gantry 10 do not move. Therefore, the projection data values of the plurality of time-series projection data sets PS1, PS2, . . . , PSn at the same position originate from X-ray paths on the same locus at different scan times.

FIG. 10 is a flowchart showing the sequence of maximum intensity projection data set generation processing. First of all, upon receiving a start request from the input unit 23 or the like, the control unit 31 causes the projection data processing unit 36 to perform maximum intensity projection data set generation processing. In the maximum intensity projection data set generation processing, first of all, the projection data processing unit 36 reads out the plurality of time-series projection data PS1 to PSn from the storage unit 40.

The projection data processing unit 36 determines a predetermined projection data value on the basis of the values of projection data PD1(i, j, k) to PDn(i, j, k) at positions (view, channel, row)=(i, j, k) in the plurality of read time-series projection data sets PS1 to PSn (step SC1). For example, the predetermined projection data value is the maximum value (maximum intensity projection data value) of the values of the projection data PD1(i, j, k ) to PDn(i, j, k).

The maximum intensity projection data value determined in step SC1 is set as a projection data value at the position (i, j, k) in the maximum intensity projection data set (step SC2).

Figure 11:
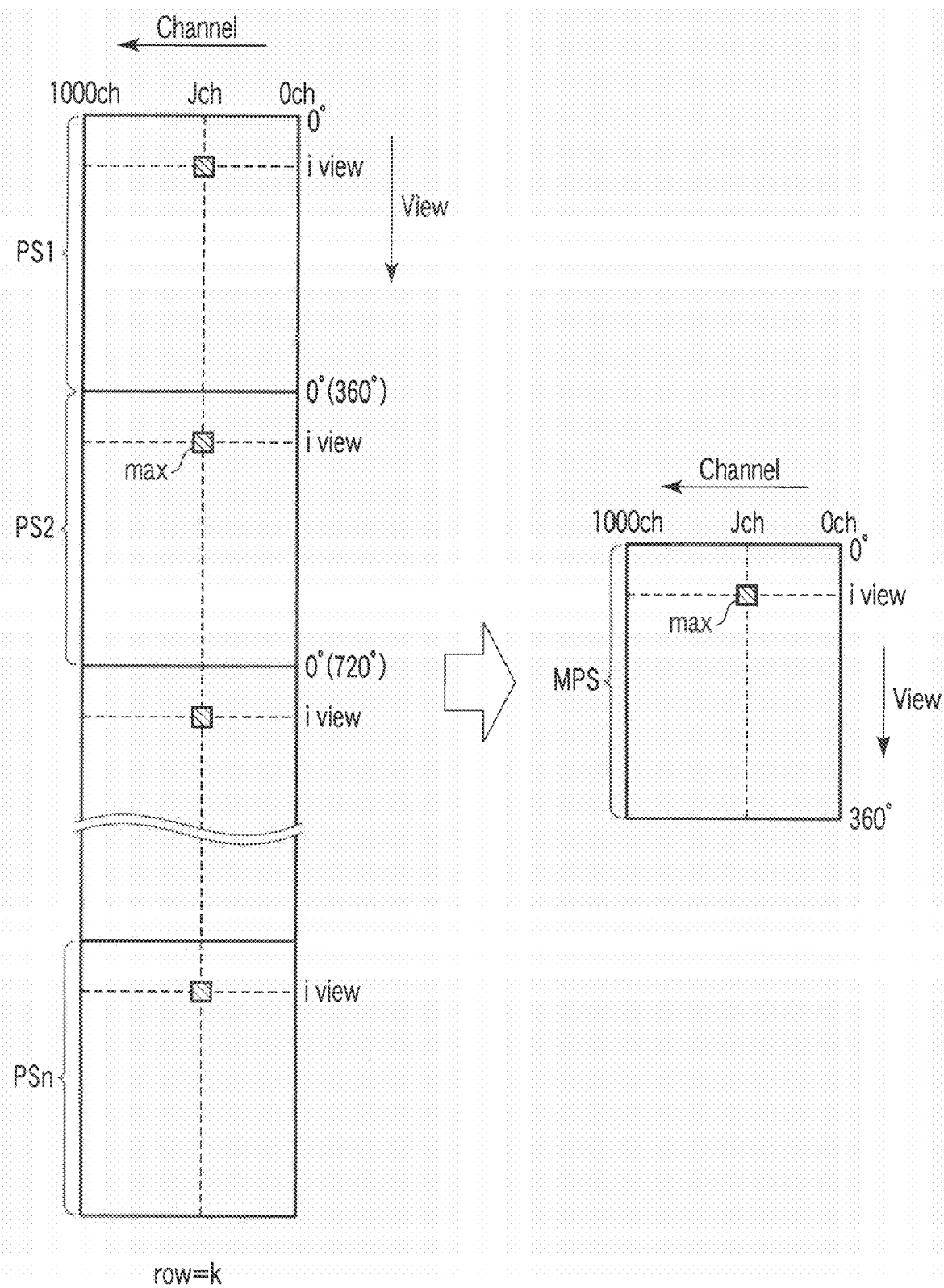
FIG. 11 is a view for explaining the processing in steps SC1 and SC2 in FIG. 10.

FIG. 11 is a view for concretely explaining the processing in steps SC1 and SC2. FIG. 11 is a view showing the time-series projection data sets (sinographs) at row=k. The time-series projection data sets shown in FIG. 11 are, for example, projection data sets in a case in which full reconstruction is used. That is, one time-series projection data set comprises a set of projection data corresponding to 0° to 360°. First of all, the projection data processing unit 36 specifies the values of the projection data PD1(i, j, k) to PDm(i, j, k) to PDn(i, j, k), of the time-series projection data sets PS1 to PSm to PSn (1<m<n), which are located at a position (e.g., [view, channel, row]=[i, j, k]). A maximum intensity projection data value is specified from the plurality of specified projection data values. The specified maximum intensity projection data value is set as a projection data value at the position (i, j, k) in the maximum intensity projection data set MPS. In the case shown in FIG. 11, the projection data value at the position (i, j, k) in the time-series projection data PS2 is maximum. This projection data value is set as a projection data value at the position (i, j, k) in the maximum intensity projection data set.

When the processing in step SC2 is complete, the projection data processing unit 36 determines whether CT values have been set at all the positions in the maximum intensity projection data set (step SC3). If determining that CT values have not been set at all the positions (NO in step SC3), the projection data processing unit 36 changes the position (i, j, k) (step SC4). The projection data processing unit 36 then performs the processing in steps SC1 and SC2 again at the position set after the position change. If this processing is performed at all the positions (YES in step SC3), projection data values are set at all the positions in the maximum intensity projection data set. That is, the maximum intensity projection data set is generated. When the maximum intensity projection data set is generated, the maximum intensity projection data set generation processing is terminated.

The reconstruction unit 34 reconstructs the generated maximum intensity projection data set into maximum intensity volume data set. The reconstructed maximum intensity volume data set is based on all the time-series projection data sets generated by 4DCT, and hence also contains information about a delay blood vessel at which a contrast agent arrives late relative to a blood vessel at which the contrast agent arrives earlier.

With the above arrangement, the X-ray CT apparatus 50 generates a single projection data set on the basis of a plurality of projection data sets. The X-ray CT apparatus 50 then generates volume data set on the basis of the generated single projection data set. According to a given aspect, simply observing only an image based on generated volume data set allows the user to obtain almost the same effect as that obtained when he/she observes a plurality of images based on a plurality of volume data sets. According to the second embodiment, therefore, the efficiency of diagnosis based on a plurality of volume data sets can be improved.

Each function associated with the first and second embodiments can also be implemented by installing programs for executing the corresponding processing in a computer such as a workstation and mapping them in a memory. In this case, the programs which can cause the computer to execute the corresponding techniques can be distributed by being stored in recording media such as magnetic disks (floppy [registered trademark] disks, hard disks, and the like), optical disks (CD-ROMs, DVDs, and the like), and semiconductor memories.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray tube which generates X-rays;
   an X-ray detector which detects X-rays generated from the X-ray tube and transmitted through an object to be examined;
   a rotating mechanism unit which continuously rotates the X-ray tube and the X-ray detector around the object;
   a reconstruction unit which reconstructs a plurality of first volume data sets with different scan times for the same scan area of the object on the basis of an output from the X-ray detector; and
   an image processing unit which generates single second volume data set corresponding to one of a maximum value, an average value, a median value, and minimum value of the plurality of reconstructed first volume data sets in a temporal direction.

2. The apparatus according to claim 1, further comprising:
   a tomogram generation unit which generates data of a tomogram on the basis of the second volume data set;
   a blood vessel extraction unit which extracts a blood vessel portion from the generated tomogram by threshold processing; and
   a display unit which superimposes and displays the extracted blood vessel portion and a functional image for an index representing a blood flow dynamic state.

3. The apparatus according to claim 2, further comprising a color information assignment unit which assigns different pieces of color information to a blood vessel portion and a tissue portion which are included in the second volume data set.

4. The apparatus according to claim 1, wherein the image processing unit generates the second volume data set by setting one of a maximum value, an average value, a median value, and a minimum value of voxel values of a plurality of voxels at the same position in the plurality of first volume data sets as a voxel value of a voxel at the same position in the second volume data set.

5. The apparatus according to claim 1, wherein the image processing unit generates the second volume data set on the basis of first volume data sets, of the plurality of first volume data sets, which concerns a predetermined period of time.

6. The apparatus according to claim 5, wherein the predetermined period of time is determined on the basis of a time density curve for a predetermined area of the plurality of first volume data sets.

7. The apparatus according to claim 1, wherein a length of the object in the scan area in a body axis direction is not less than 8 cm.

8. The apparatus according to claim 1, further comprising a control unit which controls the X-ray tube, the X-ray detector, and the rotating mechanism unit to continuously scan the same scan area of the object.

9. The apparatus according to claim 1, further comprising a selection unit which causes the image processing unit to selectively execute projection processing for a temporal direction or projection processing for a spatial direction.

10. The apparatus according to claim 1, further comprising a designation unit which designates at least one of a time range in projection processing for a temporal direction and a space range in projection processing for a spatial direction with respect to the image processing unit.

11. An X-ray computed tomography apparatus comprising:
    an X-ray tube which generates X-rays;

an X-ray detector which detects X-rays generated from the X-ray tube and are transmitted through an object to be examined;

a rotating mechanism unit which continuously rotates the X-ray tube and the X-ray detector around the object;

a reconstruction unit which reconstructs a plurality of first volume data sets with different scan times for the same scan area of the object on the basis of an output from the X-ray detector; and an image processing unit which generates single second volume set data by processing the plurality of reconstructed first volume data sets.

12. An X-ray computed tomography apparatus comprising:

an X-ray tube which generates X-rays;

an X-ray detector which detects X-rays generated from the X-ray tube and are transmitted through an object to be examined;

a rotating mechanism unit which continuously rotates the X-ray tube and the X-ray detector around the object;

a first projection data generation unit which generates a plurality of first projection data sets with different scan times for the same scan area of the object on the basis of an output from the X-ray detector;

a second projection data generation unit which generates a single second projection data set corresponding to one of a maximum value, an average value, a median value, and a minimum value of the plurality of generated first projection data sets in a temporal direction; and a reconstruction unit which reconstructs volume data set on the basis of the generated second projection data set.

13. The apparatus according to claim 12, wherein the projection data processing unit generates the second projection data set by setting one of a maximum value, an average value, a median value, and a minimum value of a plurality of projection data values of the plurality of projection data sets at the same position as a projection data value at the same position in the second projection data set.

14. An image processing apparatus comprising:

a storage unit which stores a plurality of first volume data sets with different scan times for the same scan area of an object to be examined; and an image processing unit which generates single second volume data set corresponding to one of a maximum value, an average value, a median value, and a minimum value of the plurality of first volume data sets in a temporal direction.

15. An image processing apparatus comprising:

a storage unit which stores a plurality of first projection data sets with different scan times which are generated by continuously scanning the same scan area of an object to be examined;

a projection data processing unit which generates a single second projection data set corresponding to one of a maximum value, an average value, a median value, and a minimum value of the plurality of first projection data sets in a temporal direction; and a reconstruction unit which reconstructs volume data set for the object on the basis of the generated second projection data set.

* * * * *